(12) United States Patent
Yeon et al.

(10) Patent No.: US 9,612,208 B2
(45) Date of Patent: Apr. 4, 2017

(54) APPARATUS AND METHOD OF TESTING A STICK

(71) Applicant: Samsung Display Co., Ltd., Yongin, Gyeonggi-Do (KR)

(72) Inventors: Kiyoung Yeon, Yongin (KR); Nari Ahn, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 0 days.

(21) Appl. No.: 14/608,672

(22) Filed: Jan. 29, 2015

(65) Prior Publication Data

US 2016/0084634 A1    Mar. 24, 2016

(30) Foreign Application Priority Data

Sep. 19, 2014  (KR) .................. 10-2014-0125298

(51) Int. Cl.
| | | |
|---|---|---|
| *G01B 9/04* | (2006.01) | |
| *G01B 11/06* | (2006.01) | |
| *G01N 21/94* | (2006.01) | |

(52) U.S. Cl.
CPC .............. *G01N 21/94* (2013.01); *G01B 9/04* (2013.01); *G01B 11/06* (2013.01)

(58) Field of Classification Search
USPC .... 356/237.1–241.6, 242.1–243.8, 426–431, 356/600–640
See application file for complete search history.

(56) References Cited

U.S. PATENT DOCUMENTS

| | | | | |
|---|---|---|---|---|
| 3,556,176 A | * | 1/1971 | Harding | B23Q 35/102 142/11 |
| 3,642,041 A | * | 2/1972 | Hamilton | A01G 23/097 144/338 |
| 4,945,285 A | * | 7/1990 | Gehret | H01K 1/24 313/274 |
| 5,162,941 A | * | 11/1992 | Favro | G02B 21/0032 359/235 |

FOREIGN PATENT DOCUMENTS

| | | |
|---|---|---|
| JP | 2005-085833 | 3/2005 |
| JP | 2007-139306 | 6/2007 |
| JP | 2007-139606 A | 6/2007 |
| KR | 1020040059389 A | 7/2004 |
| KR | 1020100111129 A | 10/2010 |

* cited by examiner

*Primary Examiner* — Tri T Ton
*Assistant Examiner* — Jarreas C. Underwood
(74) *Attorney, Agent, or Firm* — Robert E. Bushnell, Esq.

(57) ABSTRACT

An apparatus of testing a stick includes a tension unit that applies tension to a stick having openings formed therein and fixes the stick in place, a first testing unit that is spaced apart from the stick and tests a surface of the stick, a light dispersion unit that reflects light emitted from the first testing unit, a distance measurement unit that measures a third distance from a bottom surface of the stick to the light dispersion unit, and a control unit that calculates a second distance from a starting point of a protrusion of the stick tested by the first testing unit to the light dispersion unit, calculates a difference between the second distance and the third distance so as to calculate a height of the protrusion and determines whether the stick is defective or not, based on the height of the protrusion.

12 Claims, 5 Drawing Sheets

APPARATUS AND METHOD OF TESTING A STICK

CLAIM OF PRIORITY

This application makes reference to, incorporates the same herein, and claims all benefits accruing under 35 U.S.C. §119 from an application for APPARATUS AND METHOD OF TESTING A STICK earlier filed in the Korean Intellectual Property Office on 19 Sep. 2014 and there duly assigned Serial No. 10-2014-0125298.

BACKGROUND OF THE INVENTION

Field of the Invention

One or more exemplary embodiments relate to an apparatus and method, and more particularly, to an apparatus and method of testing a stick.

Description of the Related Art

Portable electronic devices have been widely used. Small electronic devices, such as mobile phones, and tablet personal computers (PCs) have been widely used as portable electronic devices.

In order to support various functions, such portable electronic devices include a display unit so as to provide visual information, such as an image or a video, to a user. As other components for driving the display unit recently become smaller, the proportion of the display unit to the other components in the electronic devices is gradually increasing, and a structure that may be bent to have a certain angle in a flat state has also been developed.

The display unit may include an organic light-emitting device including an organic emission layer. Various methods have been used to form the organic light-emitting device. In particular, a method of vaporizing and depositing an organic material has been used from among methods for forming the organic light-emitting device. In this case, variously shaped sticks may be used to form an organic light-emitting device having a pattern shape by vaporizing and depositing the organic material.

SUMMARY OF THE INVENTION

One or more exemplary embodiments include an apparatus and method of testing a stick.

Additional aspects will be set forth in part in the description which follows and, in part, will be apparent from the description, or may be learned by practice of the presented embodiments.

According to one or more exemplary embodiments, an apparatus for testing a stick, includes: a tension generating unit that applies tension to a stick having openings formed therein and fixes the stick in place; a first testing unit that is spaced apart from the stick and tests a surface of the stick; a light dispersion unit that is disposed in an opposite direction to that of the first testing unit based on the stick and reflects light emitted from the first testing unit; a distance measurement unit that is disposed in an opposite direction to that of the stick based on the light dispersion unit and measures a third distance from a bottom surface of the stick to the light dispersion unit; and a control unit that calculates a second distance from a starting point of a protrusion of the stick tested by the first testing unit to the light dispersion unit, calculates a difference between the second distance and the third distance so as to calculate a height of the protrusion and determines whether the stick is defective or not, based on the height of the protrusion.

The first testing unit, the light dispersion unit, and the distance measurement unit may be capable of linearly moving in a lengthwise direction of the stick.

The light dispersion unit and the distance measurement unit may be capable of moving in a vertical direction.

The apparatus may further include a pre-alignment unit that pre-aligns the stick before the stick is fixed to the tension generating unit.

The first testing unit may be a confocal microscopy system or an interferometer microscope.

The distance measurement unit may be a laser stepped system microscope, a confocal microscopy system microscope or an interferometer microscope.

The apparatus may further include a second testing unit that is capable of performing at least one selected from the group consisting of a curve test of the stick, an alien substance test, an etching degree test, a critical dimension test, a total pitch test, and a linearity test.

The apparatus may further include a recording unit that records information of the stick that is generated by the control unit based on data measured by the first testing unit and the distance measurement unit, by using a QR-code.

According to one or more exemplary embodiments, a method of testing a stick, includes: applying tension to a stick having openings formed therein and fixing the stick in place; measuring a first distance from a top surface of the stick to a light dispersion unit, a second distance from a starting point of a protrusion of the stick to the light dispersion unit, and a third distance from a bottom surface of the stick to the light dispersion unit; calculating a difference between the second distance and the third distance so as to calculate a height of the protrusion; and determining whether the stick is defective or not, based on the height of the protrusion.

The method may further include pre-aligning the stick.

The method may further include performing at least one selected from the group consisting of a curve test of the stick, an alien substance test, an etching degree test, a critical dimension test, a total pitch test, and a linearity test.

The method may further include recording information of the tested stick using a QR-code.

These general and specific aspects may be implemented by a system, a method, a computer program, or a combination of a system, a method, and a computer program.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION OF THE INVENTION

Figure 1:
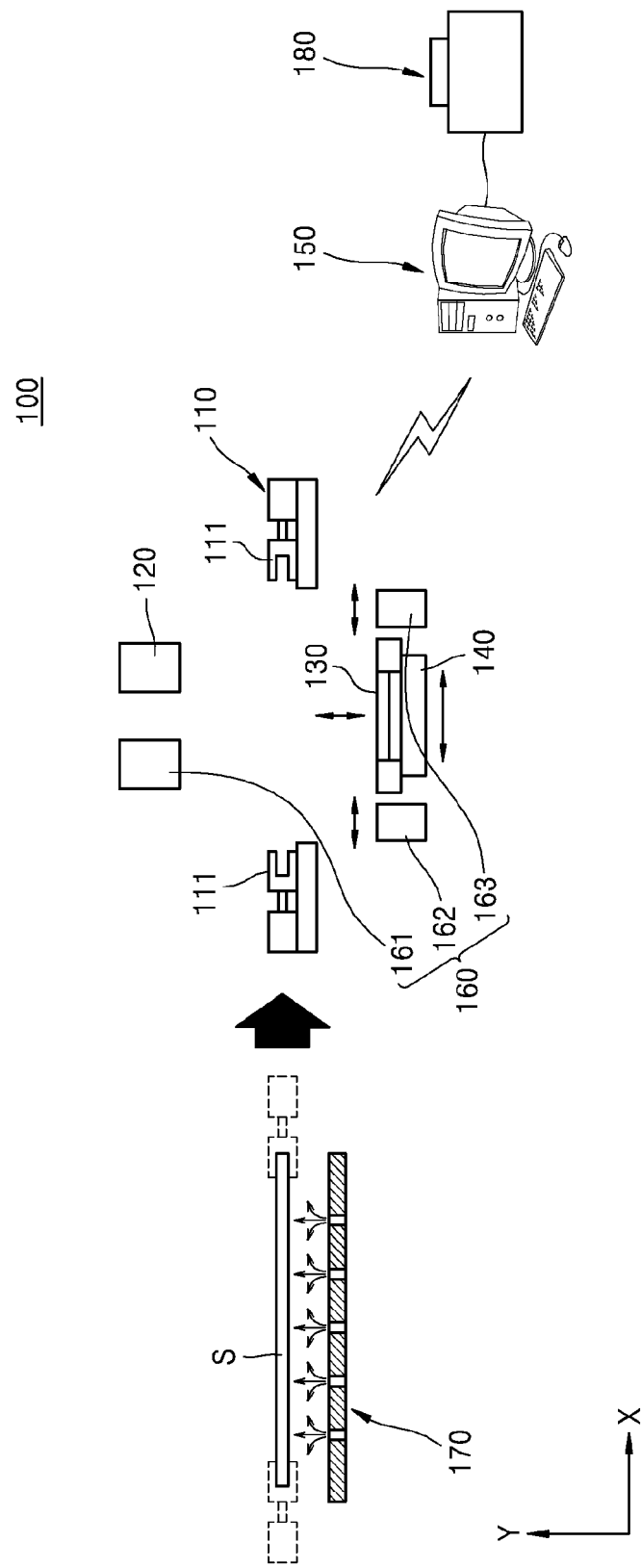
FIG. 1 is a conceptual diagram of an apparatus for testing a stick according to an exemplary embodiment.

As the invention allows for various changes and numerous embodiments, particular embodiments will be illustrated in the drawings and described in detail in the written description. The effects and features of the inventive concept, and methods for achieving them will be apparent by referring to embodiments that will be described later in detail together with the drawings. However, the inventive concept is not limited to the following embodiments but may be implemented in various shapes.

Hereinafter, exemplary embodiments of the inventive concept will be described below in more detail with reference to the accompanying drawings. Those components that are the same or are in correspondence are rendered the same reference numeral regardless of the figure number, and redundant explanations are omitted.

It will be understood that although the terms "first", "second", etc. may be used herein to describe various components, these components should not be limited by these terms. These components are only used to distinguish one component from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on," another layer, region, or component, it can be directly or indirectly formed on the other layer, region, or component. That is, for example, intervening layers, regions, or components may be present.

Sizes of elements in the drawings may be exaggerated for convenience of explanation. In other words, since sizes and thicknesses of components in the drawings are arbitrarily illustrated for convenience of explanation, the following embodiments are not limited thereto.

In the following examples, the x-axis, the y-axis and the z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

When a certain embodiment may be implemented differently, a specific process order may be performed differently from the described order. For example, two consecutively described processes may be performed substantially at the same time or performed in an order opposite to the described order. Expressions such as "at least one of," when preceding a list of elements, modify the entire list of elements and do not modify the individual elements of the list.

Figure 2:
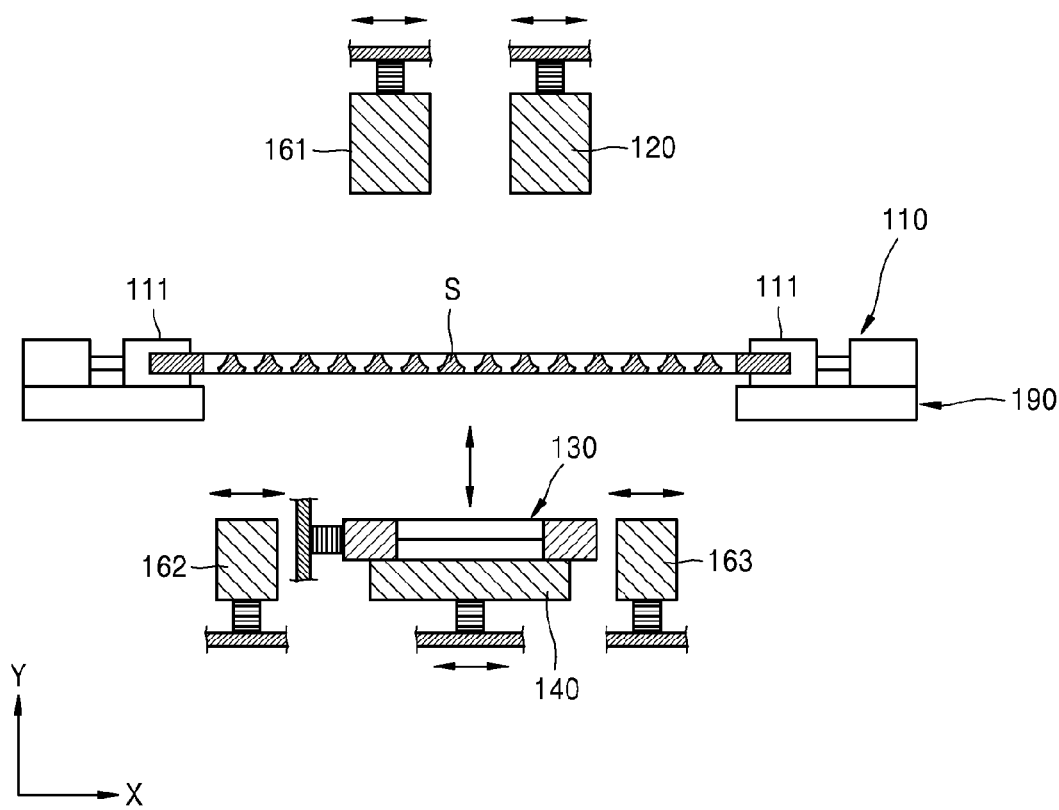
FIG. 2 is a conceptual diagram of a part of the apparatus for testing a stick illustrated in FIG. 1.
Figure 3:
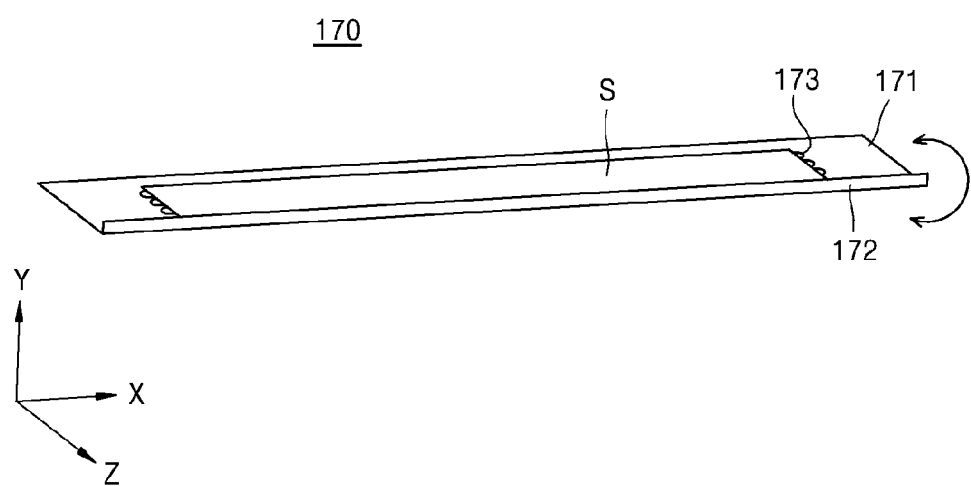
FIG. 3 is a conceptual diagram of a pre-alignment unit illustrated in FIG. 1.

FIG. 1 is a conceptual diagram of an apparatus for testing a stick according to an exemplary embodiment. FIG. 2 is a conceptual diagram of a part of the apparatus for testing a stick illustrated in FIG. 1. FIG. 3 is a conceptual diagram of a pre-alignment unit illustrated in FIG. 1.

Referring to FIGS. 1 through 3, an apparatus 100 for testing a stick may include a tension generating unit 110, a first testing unit 120, a light dispersion unit 130, a distance measurement unit 140, a control unit 150, a second testing unit 160, a pre-alignment unit 170, and a recording unit 180.

The tension generating unit 110 may fix a stick S in a tensile state. In this case, the tension generating unit 110 may be configured of a pair of clamps 111 each fixing opposite sides of the stick S. A position of the tension generating unit 110 may be changed by moving one clamp with respect to another clamp so that the stick S may be tensile. Also, the tension generating unit 110 may include a cylinder, or a gear and a motor that applies tension to the stick S by linearly moving at least one of the clamps 111. In addition, the tension generating unit 110 may include a load cell in which the clamp 111 detects a force used to cause the stick S to be tensile.

The tension generating unit 110 may fix at least one stick S in a tensile state. In this case, at least one stick S may be attached to a mask frame (not shown) or may be individually fixed to the tension generating unit 110. At least one stick S may be formed when a plurality of ribs may cross each other, and openings may be formed in the plurality of ribs that cross each other.

The above-described tension generating unit 110 may be installed to be separated from an alignment unit 190. In this case, the alignment unit 190 may have a shape in which it is moved in three different directions or in two different directions and may be rotated in one direction.

The first testing unit 120 may be disposed at a top surface of the stick S. In this case, the first testing unit 120 may be a confocal microscopy system microscope or an interferometer microscope. However, hereinafter, for convenience of explanation, a case where the first testing unit 120 is a confocal microscopy system microscope, will be described in detail. Also, the confocal microscopy system microscope is the same as or similar to a general confocal microscopy system microscope and thus, a detailed description thereof will be omitted.

The first testing unit 120 may be installed to be fixed to the top surface of the stick S or to be linearly moved. In particular, the first testing unit 120 may move linearly along a lengthwise direction of the stick S. In this case, the first testing unit 120 may be connected to the cylinder of which a length is changed. In another embodiment, as illustrated in FIG. 2, the gear and the motor may be connected to the first testing unit 120 and may move linearly according to driving of the motor.

The light dispersion unit 130 may be disposed to face the first testing unit 120 and located at the opposite side of the stick S with respect to the first testing unit 120. In this case, the light dispersion unit 130 may reflect light emitted from the first testing unit 120. Also, the light dispersion unit 130 may cause the light emitted from the distance measurement unit 140 to pass through the light dispersion unit 130.

The distance measurement unit 140 may measure a distance from a bottom surface of the stick S to the light dispersion unit 130. In this case, the distance measurement unit 140 may be one selected from the group consisting of a laser stepped system microscope, a confocal microscopy system microscope, and an interferometer microscope. In this case, the laser stepped system, the confocal microscopy system microscope, or the interferometer microscope is the same as or similar to a general laser stepped system microscope, a general confocal microscopy system microscope, and a general interferometer microscope, and thus, a detailed description thereof will be omitted. However, hereinafter, for convenience of explanation, a case where the distance measurement unit 140 is a laser stepped system, will be described in detail.

At least one of the light dispersion unit 130 and the distance measurement unit 140 may move linearly. In this case, at least one of the light dispersion unit 130 and the distance measurement unit 140 may move linearly in the lengthwise direction of the stick S. However, hereinafter, for convenience of explanation, a case where the light dispersion unit 130 and the distance measurement unit 140 are formed integrally with each other and are simultaneously moved, will be described in detail.

The light dispersion unit 130 and the distance measurement unit 140 described above may be moved in the lengthwise direction of the stick S as well as in a vertical direction perpendicular to the lengthwise direction of the stick S. In detail, the light dispersion unit 130 and the distance measurement unit 140 may be vertically moved based on the distance from the bottom surface of the stick S to the light dispersion unit 130 that is measured by the distance measurement unit 140.

In this case, a cylinder that linearly moves the clamp 111 in the lengthwise direction of the stick S and a cylinder that linearly moves the clamp 111 in the vertical direction may be connected to at least one of the light dispersion unit 130 and the distance measurement unit 140. In another embodiment, as illustrated in FIG. 2, the gear and the motor may be connected to at least one of the light dispersion unit 130 and the distance measurement unit 140 and may move linearly in each direction.

The control unit 150 may control each of elements of the apparatus 100 for testing a stick. In this case, the control unit 150 may determine whether the stick S is defective or not based on the result of measurement using the first testing unit 120 and the second testing unit 160.

The control unit 150 may be formed in various shapes. For example, the control unit 150 may include terminal equipment, a personal computer (PC), a notebook computer, and a personal digital assistant (PDA), which are installed at an outer portion of the apparatus 100 for testing a stick. Also, the control unit 150 may include a printed circuit board (PCB) installed in the apparatus 100 for testing a stick.

The second testing unit 160 may test whether the stick S is defective or not, using various methods. In this case, the second testing unit 160 may perform at least one from among a curve test of the stick S, an alien substance test, an etching degree test, a critical dimension test, a total pitch test, and a linearity test. For example, the second testing unit 160 may include a curve tester 161 that tests a degree of bending and damage information of the stick S. In this case, the curve tester 161 may be disposed to be parallel to the first testing unit 120 so that a path of the curve tester 161 and a path of the first testing unit 120 may not overlap each other. Since the curve tester 161 may be formed to be the same as or similar to a general curve tester, a detailed description thereof will be omitted.

The second testing unit 160 may include a line scanner 162 that tests whether an alien substance is attached to the stick S or whether etching of the stick S is defective. In this case, the line scanner 162 may determine whether the stick S is defective or not, by irradiating laser onto the stick S.

Also, the second testing unit 160 may include an area camera 163 that performs at least one of a critical dimension test, a total pitch test, and a linearity test of the stick S. In this case, the area camera 163 may generate an image by capturing an image of the stick S and may determine whether the stick S is defective or not based on the image using the control unit 150.

The line scanner 162 and the area camera 163 described above may be disposed to face the first testing unit 120. That is, the first testing unit 120 may be disposed at the top surface of the stick S, and the line scanner 162 and the area camera 163 may be disposed at the bottom surface of the stick S. In this case, the line scanner 162 and the area camera 163 may be disposed so that their paths may not overlap the distance measurement unit 140.

A cylinder, of which the length is changed, may be connected to the curve tester 161, the line scanner 162, and the area camera 163 and may move linearly. In another embodiment, as illustrated in FIG. 2, the motor and the gear may be connected to the curve tester 161, the curve tester 161, the line scanner 162, and the area camera 163 and may move linearly.

The pre-alignment unit 170 may pre-align the stick S. In detail, the pre-alignment unit 170 may include a stage 171 on which the stick S is seated, and a block 172 that is installed to be perpendicular to the stage 171. Also, the pre-alignment unit 170 may include a floating portion 173 that is installed at the stage 171 and discharges air so as to cause the stick S to float. In this case, the pre-alignment unit 170 may be rotatably installed and thus may pre-align the stick S.

The pre-alignment unit 170 may include an absorption pad (not shown) that is installed to protrude from the stage 171 and absorbs both ends of the stick S, instead of the floating portion 173. In this case, the absorption pad may absorb and fix a part of the stick S.

The recording unit 180 may record information, such as testing information of the stick S and basic information of the stick S, using a QR-code. In this case, the recording unit 180 may include all devices that generate the QR-code and attach the OR code to the stick or generate the QR-code directly in the stick S.

The first testing unit 120 and the tension generating unit 110 described above may move relative to each other. Also, the second testing unit 160 and the tension generating unit 110, the pre-alignment unit 170 and the tension generating unit 110, and the light dispersion unit 130 and the tension generating unit 110 may move relative to each other.

For example, the tension generating unit 110 may be installed to be fixed to the apparatus 100 for testing a stick, and the first testing unit 120, the second testing unit 160, the pre-alignment unit 170, and the light dispersion unit 130 may be installed to move linearly. In this case, when the stick S is fixed to the tension generating unit 110, the first testing unit 120, the second testing unit 160, the pre-alignment unit 170, and the light dispersion unit 130 may move to the top surface or the bottom surface of the stick S fixed to the tension generating unit 110 and may perform each of the following operations. Also, the first testing unit 120, the second testing unit 160, the pre-alignment unit 170, and the light dispersion unit 130 may move linearly, as described above, in positions in which they move individually.

In another embodiment, the tension generating unit 110 may be installed to move linearly, and the first testing unit 120, the second testing unit 160, the pre-alignment unit 170, and the light dispersion unit 130 may be installed to be fixed to the apparatus 100 for testing a stick, the first testing unit 120, the second testing unit 160, the pre-alignment unit 170, and the light dispersion unit 130 may be installed to move linearly, as described above, in fixed positions.

Hereinafter, for convenience of explanation, a case where the tension generating unit 110 is installed to move linearly, will be described in detail.

Hereinafter, a method of testing the stick S using the apparatus 100 for testing the stick S will be described in detail.

Figure 4:
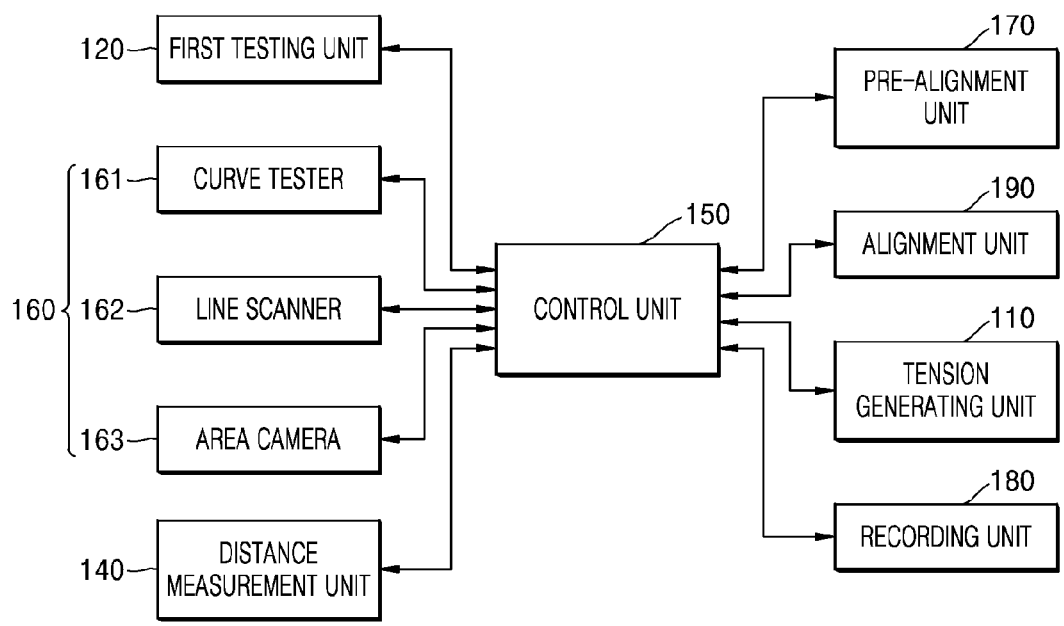
FIG. 4 is a block diagram of a flow chart for testing a stick of FIG. 1.
Figure 5:
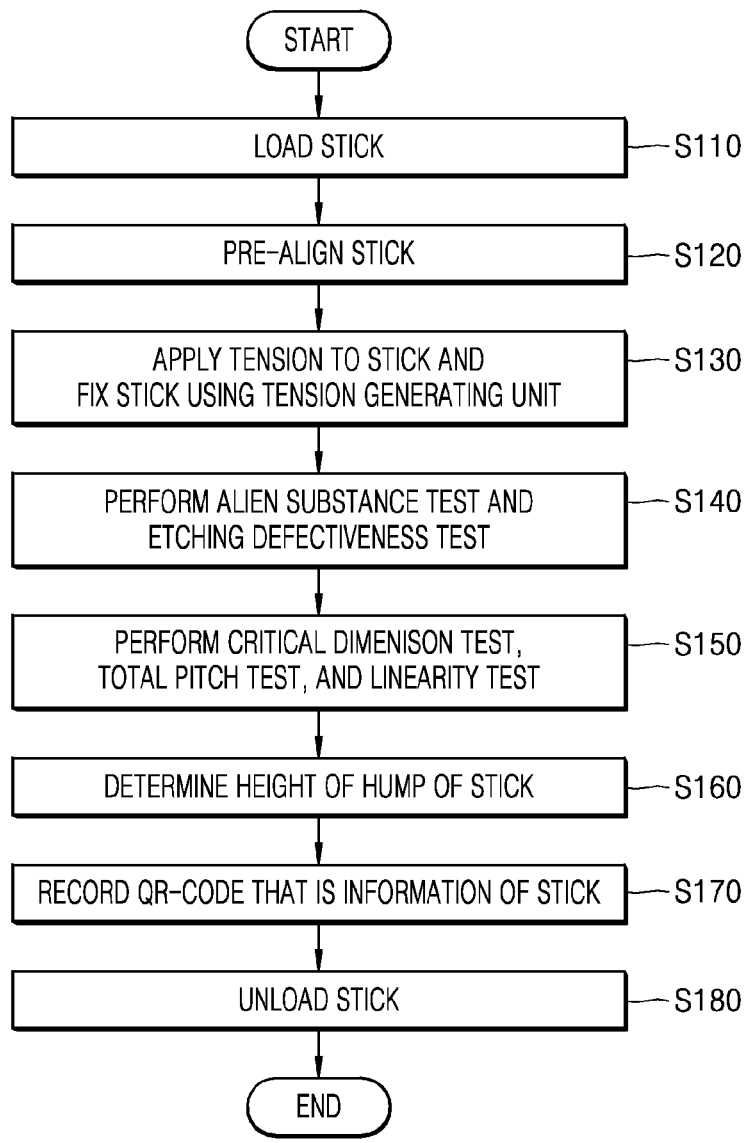
FIG. 5 is a flowchart of a method of testing a stick using the apparatus for testing a stick of FIG. 1.
Figure 6:
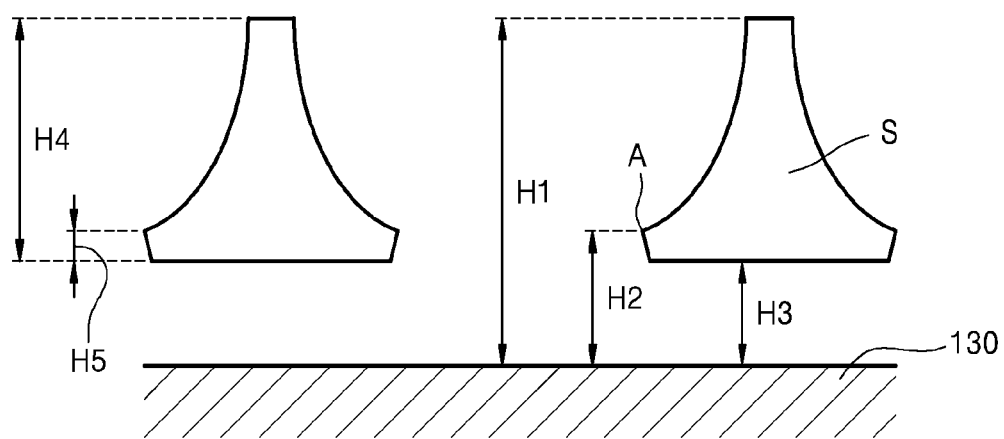
FIG. 6 is a conceptual diagram of a height of a protrusion of a stick illustrated in FIG. 1.

FIG. 4 is a block diagram of a flow chart for testing the stick S illustrated in FIG. 1. FIG. 5 is a flowchart of the method of testing the stick S using the apparatus 100 for testing the stick S. FIG. 6 is a conceptual diagram of a height of a protrusion of the stick S of FIG. 1.

Referring to FIGS. 4 through 6, when the apparatus 100 for testing a stick operates, the stick S may be taken out from a stick storage unit (not shown) and may be seated on the pre-alignment unit 170 (Operation S110). In this case, when the stick S is seated on the pre-alignment unit 170, the floating portion 173 may discharge the air toward the stick S and may cause the stick S to be spaced apart from the stage 171. Subsequently, the stage 171 may be rotated at a predetermined angle, and the stick S may be rotated together with the stage 171, may be in contact with the block 172 and thus may be primarily aligned (Operation S120).

In this case, when the pre-alignment unit 170 includes the absorption pad, the stick S that is inserted from the outside may be seated on the absorption pad and thus may be attached thereto. In particular, in the above case, before the stick S is seated on the absorption pad, a position of the stick S and a position of the stage 171 of the pre-alignment unit 170 are detected by capturing an image of the stick S and an image of the stage 171 of the pre-alignment unit 170 and then, the position of the stick S is aligned so that the stick S may be primarily aligned. However, hereinafter, a case where, after the stick S is seated on the stage 171, as described above, the stick S is rotated together with the stage 171 and thus is in contact with the block 172 and thus is pre-aligned, will be described in detail.

Subsequently, the tension generating unit 110 may be moved to the pre-alignment unit 170 so as to fix both ends of the stick S. The tension generating unit 110 may be moved to an initial position from the pre-alignment unit 170 and thus may fix the stick S in a tensile state. In this case, a load cell is disposed at the tension generating unit 110 so that the stick S may be tensile with a predetermined force (Operation S130).

If tension is completed, as described above, the control unit 150 may control the alignment unit 190 to align the tension generating unit 110 in a set position. In this case, an operation of aligning the tension generating unit 110 using the alignment unit 190 is the same as or similar to an operation of aligning a substrate or a mask in the field of a general display and thus, a detailed description thereof will be omitted.

As described above, if fixing of the stick S is completed, the second testing unit 160 may test the stick S. In detail, a bending degree of the stick S may be tested using the curve tester 161. In this case, a three-dimensional (3D) laser testing system may be used as the curve tester 161 (Operation S130).

The control unit 150 may determine whether the stick S is defective or not, by comparing the bending degree of the stick S measured by the curve tester 161 with the predetermined value. In this case, when the bending degree of the stick S has a normal value, the control unit 150 may control the line scanner 162 to perform the following test.

The line scanner 162 may be disposed at the bottom surface of the stick S and may measure whether an alien substance is attached to the stick S and whether etching of the stick S is defective or not. In this case, the control unit 150 may determine whether the alien substance is attached to the stick S and whether etching of the stick S is defective or not, by comparing the value measured by the line scanner 162 with the predetermined value (Operation S140).

If it is determined by the control unit 150 that there is no abnormality, based on the value measured by the line scanner 162, the control unit 150 may control the area camera 163 to capture an image of the stick S and may perform a critical dimension test, a total pitch test, and a linearity test based on the captured image of the stick S. In this case, the critical dimension test may be a test regarding whether a length of a diagonal line of each of openings is accurate in a predetermined region, and the total pitch test may be a test of the entire length of a region including a predetermined number of openings. Also, the linearity test may be a test regarding whether the openings are arranged in a predetermined line (Operation S150).

If it is determined that the stick S is in a normal state from the above-described result, the control unit 150 may perform a test of a height H5 of a protrusion of the stick S that is the following operation. In this case, the height H5 of the protrusion of the stick S may be defined, as illustrated in FIG. 6. That is, a cross-section of the other portions of the stick S than the openings thereof may be formed, as illustrated in FIG. 6. In this case, a width of the stick S is increased as the stick S is closer to the top surface from the bottom surface and then is uniform or decreased after a predetermined amount of time elapses. In this case, a portion of the stick S having a uniform width or a decreased width may be determined as a protrusion of the stick S, and a height of the portion of the stick S may be defined as the height H5 of the protrusion of the stick S.

The height H5 of the protrusion of the stick S may greatly affect defectiveness of a shadow when an organic material is deposited onto the stick S. Thus, precisely measuring the height H5 of the protrusion of the stick S is significantly important to improve accuracy and precision of organic material deposition.

In order to check this, in the related art, an image of a cut portion of the stick S is captured after cutting the stick S, or the height H5 of the protrusion of the stick S is measured using a microscope. However, in this case, the entire used stick S need to be tested, and after the stick S is cut, the cut portion of the stick S is discarded such that the stick S may not be used. In addition, when the related art described above is used, a working time is long so that productivity may be lowered.

Thus, the apparatus 100 for testing a stick according to the one or more exemplary embodiments tests the stick S in a noncontact manner, thereby preventing productivity from being lowered and minimizing deformation of the stick S.

In detail, after various tests are completed, as described above, the control unit 150 may acquire a 3D image of the stick S using the first testing unit 120. In this case, the control unit 150 may calculate a first distance H1 from the light dispersion unit 130 to the top surface of the stick S from the above-described image. Also, the control unit 150 may calculate a second distance H2 from the light dispersion unit 130 to a starting point A of the hum of the stick S.

While the above-described work is performed, the distance measurement unit 140 may measure a third distance H3 from the light dispersion unit 130 to the bottom surface of the stick S. In this case, measuring the first testing unit 120 and the distance measurement unit 140 may be repeatedly performed at an arbitrary portion of the stick S several times.

Also, while the above-described work is performed, the control unit 150 may move the light dispersion unit 130 and the distance measurement unit 140 vertically so that the third distance H3 may be the same as a predetermined distance. In this case, the light dispersion unit 130 and the distance measurement unit 140 may be connected to the cylinder or the gear and the motor and thus may move vertically.

If the above-described work is completed, the control unit 150 may calculate a difference between the first distance H1 and the third distance H3, thereby calculating the entire height H4 of the stick S. Also, the control unit 150 may calculate the height H5 of the protrusion of the stick S by calculating a difference between the second distance H2 and the third distance H3. The control unit 150 may determine whether the stick S is defective or not, by calculating the height H5 of the protrusion of the stick S and then comparing the calculated height 5 of the protrusion of the stick S with a predetermined value (Operation S160).

The control unit 150 may control the recording unit 180 to record various information described above in the stick S. The recording unit 180 may generate a QR-code on the stick S, may attach the generated QR-code to the stick S or may record the QR-code in the stick S. In this case, various information including an identification number of the stick S, a material used for forming the stick S, characteristics of the stick S, defectiveness of the stick S, the result of testing the stick S, the manufacturing date of the stick S, and a manufacturer of the stick S, may be associated with the QR-code (Operation S170).

If the above-described operation is completed, the stick S may be again transferred to the stick storage unit or may be taken out toward the outside. In this case, depending on whether the stick S is defective or not, the normal stick S and the defective stick S may be transferred to be distinguished from each other (Operation S180).

Thus, in the apparatus 100 and method of testing a stick, the stick S may be tested in a noncontact manner so that productivity may be lowered and deformation of the stick S may be minimized.

Also, in the apparatus 100 and method of testing a stick, the height of the protrusion is measured in a nondestructive manner so that a measurement time may be reduced and 100% testing of the stick S may be performed.

As described above, in an apparatus and method of testing a stick according to the one or more of the above exemplary embodiments, an accurate and precise stick test may be performed.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for testing a stick, comprising:
a tension generator fixing a stick having openings formed therein and applying tension to the stick;
a first tester disposed spaced-apart from the stick and testing a surface of the stick;
a light disperser disposed in an opposite side of the first tester based on the stick and reflecting light emitted from the first tester;
a distance measurer disposed in an opposite direction to that of the stick based on the light disperser and determining a third distance from a bottom surface of the stick to the light disperser; and
a controller determining a second distance from a starting point of a protrusion of the stick tested by the first tester to the light disperser, determining a difference between the second distance and the third distance so as to determine a height of the protrusion, and determining whether the stick is defective or not, based on the height of the protrusion.

2. The apparatus of claim 1, wherein the first tester, the light disperser, and the distance measurer are capable of linearly moving in a lengthwise direction of the stick.

3. The apparatus of claim 1, wherein the light disperser and the distance measurer are capable of moving in a vertical direction perpendicular to the lengthwise direction of the stick.

4. The apparatus of claim 1, further comprising a pre-aligner that pre-aligns the stick before the stick is fixed to the tension generator.

5. The apparatus of claim 1, wherein the first tester is a confocal microscopy system or an interferometer microscope.

6. The apparatus of claim 1, wherein the distance measurer is a laser stepped system microscope, a confocal microscopy system microscope or an interferometer microscope.

7. The apparatus of claim 1, further comprising a second tester performing at least one selected from the group consisting of a curve test of the stick, an alien substance test, an etching degree test, a critical dimension test, a total pitch test,and a linearity test.

8. The apparatus of claim 1, further comprising recorder that records information of the stick that is generated by the controller based on data measured by the first tester and the distance measurer, by using a QR-code.

9. A method of testing a stick, comprising:
applying tension to a stick having openings formed therein and fixing the stick in place;
determining a first distance from a top surface of the stick to a light disperser, a second distance from a starting point of a protrusion of the stick to the light disperser, and a third distance from a bottom surface of the stick to the light disperser;
determining a difference between the second distance and the third distance so as to calculate a height of the protrusion; and
determining whether the stick is defective or not, based on the height of the protrusion.

10. The method of claim 9, further comprising pre-aligning the stick.

11. The method of claim 9, further comprising performing at least one selected from the group consisting of a curve test of the stick, an alien substance test, an etching degree test, a critical dimension test, a total pitch test, and a linearity test.

12. The method of claim 9, further comprising recording information of the tested stick using a QR-code.

* * * * *